United States Patent [19]

Lee

[11] Patent Number: 5,733,562
[45] Date of Patent: Mar. 31, 1998

[54] INJECTABLE MEDICAL DEVICE AND METHOD OF USE

[75] Inventor: Clarence C. Lee, Lilburn, Ga.

[73] Assignee: C.R. Bard, Inc., Murray Hill, N.J.

[21] Appl. No.: 465,676

[22] Filed: Jun. 6, 1995

Related U.S. Application Data

[63] Continuation of Ser. No. 117,880, Sep. 7, 1993, Pat. No. 5,639,796, which is a continuation of Ser. No. 940,775, Sep. 4, 1992, abandoned, which is a continuation of Ser. No. 654,773, Feb. 12, 1991, abandoned.

[51] Int. Cl.$^6$ ...................................................... A61K 9/107
[52] U.S. Cl. ................... 424/422; 514/772.2; 514/772.3
[58] Field of Search ............................... 514/772.2, 772.3

[56] References Cited

U.S. PATENT DOCUMENTS

| | | |
|---|---|---|
| Re. 32,969 | 6/1989 | Trager et al. . |
| 3,697,653 | 10/1972 | Ongley . |
| 4,197,846 | 4/1980 | Bocalo . |
| 4,503,034 | 3/1985 | Maupetit et al. . |
| 4,631,188 | 12/1986 | Stoy et al. ............... 424/78.1 |
| 4,725,442 | 2/1988 | Haynes . |
| 4,775,659 | 10/1988 | Thakkar et al. . |
| 4,777,200 | 10/1988 | Dymond et al. ............... 524/458 |
| 4,803,075 | 2/1989 | Wallace et al. . |
| 4,822,368 | 4/1989 | Collier . |
| 4,828,828 | 5/1989 | Trager et al. . |
| 4,867,970 | 9/1989 | Newsham et al. . |
| 4,883,864 | 11/1989 | Scholz . |
| 4,913,903 | 4/1990 | Sudmann et al. . |
| 4,943,618 | 7/1990 | Stoy et al. . |
| 5,007,940 | 4/1991 | Berg ............................... 623/66 |
| 5,156,839 | 10/1992 | Pennell et al. . |
| 5,166,331 | 11/1992 | della Valle et al. . |
| 5,171,566 | 12/1992 | Mizushima et al. . |
| 5,264,214 | 11/1993 | Rhee et al. . |
| 5,304,595 | 4/1994 | Rhee et al. . |
| 5,328,955 | 7/1994 | Rhee et al. . |
| 5,376,375 | 12/1994 | Rhee et al. . |
| 5,484,601 | 1/1996 | O'Leary et al. ............... 514/772.2 |

FOREIGN PATENT DOCUMENTS

| | | |
|---|---|---|
| 0 144 019 A2 | 6/1985 | European Pat. Off. . |
| 0144019 | 6/1985 | European Pat. Off. . |
| 0 301 966 A2 | 2/1989 | European Pat. Off. . |
| 0 499 164 A1 | 8/1992 | European Pat. Off. . |
| 2059506 | 6/1971 | France . |
| 90/04971 | 5/1990 | WIPO . |
| 9004971 | 5/1990 | WIPO . |

OTHER PUBLICATIONS

Andrade, Ed., *Hydrogels for Medical and Related Applications*, American Chemical Society, Washington, D.C., pp. 6–36 and 329–342 (1976).

*Primary Examiner*—Thurman K. Page
*Attorney, Agent, or Firm*—Jones & Askew, LLP

[57] ABSTRACT

The present invention is an injectable medical device useful for replacing natural lubricating fluids in the body of humans or animals. The method and composition can be used for the treatment of joints and other parts of the body wherein natural lubrication between surfaces is deficient or where additional lubrication is required. The composition comprises a hydrophilic polymer suspended in a hydrophobic carrier so that the suspension is easily injectable into the desired body part. After injection, the carrier diffuses away from the polymer and is replaced by aqueous body fluids thereby causing the polymer to absorb or adsorb water forming a viscous, lubricating fluid.

12 Claims, No Drawings

INJECTABLE MEDICAL DEVICE AND METHOD OF USE

This is a continuation, of application Ser. No. 08/117,880, filed Sep. 7, 1993 and now U.S. Pat. No. 5,639,796 which is a continuation of Ser. No. 07/940,775 filed Sep. 04, 1992 now abandoned which is a continuation of Ser. No. 07/654,773, filed Feb. 12, 1991 and now abandoned.

FIELD OF THE INVENTION

The present invention relates to a method and composition for the treatment of joints and other parts of the body wherein natural lubrication between surfaces is deficient or where additional lubrication is required. In particular, the present invention is an easily injectable composition comprising a hydrophilic lubricating polymer suspended in a hydrophobic liquid.

BACKGROUND OF THE INVENTION

The skeletal system of humans and animals consists of bones and joints to which are attached muscles, tendons and ligaments. Bones are the principal organs of support and protection for the body. Joints are the places at which two bones meet (articulate). Because bones are incapable of movement without the help of muscles, contraction must be provided by muscular tissue. In the skeleton, muscles are usually attached to two articulating bones, and during contraction, one bone is drawn toward another. Muscles, therefore produce movement by exerting a force on the bones to which they are attached.

Bones consist of mineral deposits embedded with living cells that must continually receive food and oxygen. Bones generally consist of the following parts. The diaphysis is the shaft or long main portion of the bone. This part of the bone consists mainly of compact bone. The epiphyses are the two ends or extremities of the bone. In the long bones, the epiphyses have a bulbous shape to provide space for muscle and ligament attachments near the joints. Articular cartilage is a thin layer of resilient hyaline cartilage. The elasticity of the hyaline cartilage provides the joints with a cushion against jars and blows.

To allow body movements, all bones must have articulating surfaces. These surfaces form joints, or articulations, with various degrees of mobility. Some are freely movable (diarthroses); others are only slightly movable (amphiarthroses); and the remaining are totally immovable (synarthroses). All three types are necessary for smooth, coordinated body movements.

Every joint is covered with connective tissue and cartilage. The ligaments and connective tissue in these areas permit bones to be connected to each other. Muscles attached to freely movable joints permit a great deal of body movement. The synovial membrane that lines the joint cavity secretes synovial fluid, which acts as a lubricant of the joints. The bones in a synovial joint are separated by a joint capsule. The joint capsule is strengthened by ligaments (fibrous bands, or sheets, of connective tissue) that often anchor bones to each other. All of the above factors working together in a complementary manner make various body movements possible.

Thus, the joints of humans and animals comprise two or more bone surfaces that are in constant contact with each other. These surfaces slide against each other as the joint is moved. Because the pressures on the surfaces can be enormous and the movement is constant, a highly efficient lubricating system is necessary to prevent the deterioration of the bone surface. This is done naturally by coating the contacting surfaces with a layer of collagen-like material which reduces the friction caused by the constant contact and motion between the surfaces. In addition, a natural aqueous lubricating liquid, called synovial fluid, is normally present which further reduces the friction between the surfaces in the joint.

The aqueous lubricating synovial fluid is a solution containing a heteropolysaccharide such as hyaluronic acid. Hyaluronic acid contains alternating residues of two different sugar units. These alternating units am normally D-glucuronic acid and N-acetyl-D-glucosamine. Hyaluronic acid forms a highly viscous jelly-like solution which is ideal for lubricating a joint in an animal or human.

In certain abnormal conditions, the natural lubricating fluid is present in abnormally low amounts resulting in painful joints. In these conditions, it is common to prepare a solution of hyaluronic acid, collagen, or other types of synthetic or natural high-viscosity material. These solutions are then injected into the abnormal joint to aid in the lubrication of the joint surfaces during movement.

Aqueous solutions of water-soluble viscoelastic polymers have been widely used to lubricate joints such as knee joints, spinal cord or other areas of the body. These solutions minimize physical trauma due to surface abrasion. In the joints, the solutions lubricate the contact surfaces as the synovial fluid in the normal joints. Traditionally, a dilute solution (0.1 to 5% w/v) has been used because of the handling convenience. Because the concentrated aqueous solution is an extremely viscous gel, it is quite difficult to inject the material through a 14-gauge needle.

Thus, a major problem in administering these solutions is the extremely high viscosity of the solutions. It is very difficult to inject high concentrations or large amounts of these viscous materials into body tissues, such as joints or urethral soft tissues. Very large gauge needles are required to administer sufficient quantities of the the fluid to the intended body pan. This results in extreme discomfort to the human or animal to which the fluid is being administered. Depending on the compound used and the concentration of the compound, the injectability of the suspension may be less than adequate. Such inadequacy may manifest itself in terms of difficulties in extruding the suspension through a fine gauge needle and/or poor intrusion into the tissue. Common extrusion difficulties are excessive or irregular extrusion pressures and needle blockage.

What is needed is a delivery system that will enable the physician or veterinarian to inject the material in relatively small volumes using small gauge needles. Ideally, the delivery system should include a solution which is not viscous, but will develop desired physical properties after it has been delivered to the desired site in the body.

SUMMARY OF THE INVENTION

The present invention is a composition comprising a suspension of fine hydrophilic polymer powder in a hydrophobic carrier. The suspension is very fluid and can be easily extruded through a narrow gauge needle. After injection into the desired body part, the hydrophobic carrier diffuses away from the polymer and the polymer either absorbs or adsorbs water molecules from body fluids. This process ideally occurs gradually and the polymer then exhibits the desired lubricating properties. The carrier is non-toxic and is easily eliminated from the body after injection. The carriers can be selected from nontoxic liquid polymers, liquid surfactants, liquid plasticizers, and solvents.

The lipophobic viscoelastic polymer should ideally be in the form of beads or particles in the range of between approximately 4 to 150 microns in diameter. The polymer beads or particles do not necessarily have to be uniform in size or shape. The beads are suspended in the carrier and, because of the lack of water, the beads retain their shape. The polymer can be either a natural polymer or a synthetic polymer. Examples of natural polymers include, but are not limited to, chondroitin sulfate, hyaluronic acid, cellulose, agarose, chitin, dextran, carrageenin, collagen, elastin, peptides and growth factors, and cross-linked elastin and hyaluronic acid or combinations thereof. Growth factors that can be used in the present invention include, but are not limited to, nerve growth factor, colony stimulating factor, macrophage stimulating factor, granulocyte stimulating factor, macrophage/granulocyte stimulating factor, platelet-derived growth factor and fibroblast growth factor or combinations thereof. Examples of synthetic polymers include, but is not limited to, methylcellulose, hydroxypropylmethylcellulose, polyacrylonitrile polymer, polyethylene, glycolpolyurethane, hydrophilic polyurethane (sold under the tradename Hypol® polymer, W. R. Grace, New York, N.Y.), polyvinylpropylene, poly(2-hydroxyethyl methacrylate), polyleucine, polylysine, poly(ethylene-vinylalcohol) copolymer, and cross-linked polyvinylpropylene and poly-L-lysine or combinations thereof.

In the method contemplated as part of the present invention, a composition comprising a suspension of fine polymer powder and hydrophobic carrier is injected into the desired body part. After injection into the body, the hydrophobic carrier diffuses away from the polymer. The polymer then takes on the physical properties which are required for a good lubricant.

Accordingly, it is an object of the present invention to provide a composition that can be easily injected into an animal or human to provide lubricant for a joint or other part of the body.

Another object of the present invention is to provide a method for treating any condition in an animal or human wherein there is a deficiency of lubricating substance in a joint.

Another object of the present invention is to provide a composition that can be used to treat symptoms of arthritis.

Yet another object of the present invention is to provide a composition that can be administered to urethral soft tissue.

Another object of the present invention is to provide a composition and method for treating degenerative joint diseases such as osteoarthrosis, chondrocalcinosis, gout and traumatic synovitis.

Another object of the present invention is to provide a composition and method for treating cutaneous imperfections, such as depressions and scars.

Another object of the present invention is to provide a composition that can be administered to urethra, periurethral tissue or submucosa of the bladder for treating urinary incontinence, viscourethral reflux and other urinary tract symptoms and/or diseases.

Yet another object of the present invention is to provide a composition that can be administered to the esophageal sphincter for treating esophageal reflux.

Another object of the present invention is to provide a composition that can be injected into the vocal cord for the correction of deformed vocal cords.

Another object of the present invention is to provide a composition that can be injected into membranous implants in situ to inflate them.

Another object of the present invention is to provide a composition that can be injected into vessels such as the vas deferans to cause permanent blockage at the implant site.

These and other objects, features and advantages of the present invention will become apparent after a review of the following detailed description of the disclosed embodiment and the appended claims.

DETAILED DESCRIPTION OF THE INVENTION

The present invention is a composition comprising a suspension of a fine polymer powder in a hydrophobic liquid carrier. The present invention also includes a method of administering a composition comprising a suspension of a fine polymer powder in a hydrophobic liquid carrier to a human or animal that requires lubrication in a joint or other body part.

The polymer powder can be any hydrophilic polymer which, when placed in contact with water, acquires lubricating properties. The polymer can be in the form of beads or irregular particles. The term "particle" is intended to include both fibrous and nonfibrous polymers. Preferably, the particles should be between approximately 4 microns and 150 microns in diameter. However, the particle size can be outside the preferred range and still be within the contemplated invention. The polymer powder should be a suspension of the solid polymer in the liquid hydrophobic carrier. In some cases, some water may be present in the carrier but it is important that not enough water be present to cause the polymer to swell significantly thereby causing the solution to become viscous and difficult to administer to the human or animal.

The injectable device which comprises the present invention is capable of being sterilized by conventional techniques that are commonly used in the manufacture of pharmaceuticals and medical devices such as autoclaving, filtering or irradiation.

The polymer can be a natural polymer or it can be synthetic polymer. Examples of natural polymers include, but are not limited to, chondroitin sulfate, hyaluronic acid, cellulose, agarose, chitin, dextran, carrageenin, collagen, elastin, peptides and growth factors, and cross-linked elastin and hyaluronic acid. Other sulfated mucopolysaccharides can also be used in the present invention or combinations thereof. Growth factors that can be used in the present invention include, but are not limited to, nerve growth factor, colony stimulating factor, macrophage stimulating factor, granulocyte stimulating factor, macrophage/granulocyte stimulating factor, platelet-derived growth factor and fibroblast growth factor or combinations thereof. It should be noted that the molecular weights of the polymers can vary widely from one hundred thousand daltons to three million daltons. Typically, the polymers will be present as a mixture of molecules of varying molecular weights or combinations thereof.

Examples of synthetic polymers include, but is not limited to, methylcellulose, hydroxypropylmethylcellulose, polyacrylonitrile polymer, polyethylene, glycolpolyurethane, hydrophilic polyurethane (sold under the tradename Hypol® polymer, W. R. Grace, New York, N.Y.), polyvinylpropylene, poly(2-hydroxyethyl methacrylate), polyleucine, polylysine, poly(ethylene-vinylalcohol) copolymer, and cross-linked polyvinylpropylene and poly-L-lysine. The synthetic polymers will typically be made up of a mixture of molecules of varying molecular weights. It is also possible to have mixtures of different kinds of polymers as well as mixtures of synthetic polymers and natural polymers.

The carrier is preferably a hydrophobic liquid. It is important in the present invention that the polymer that is suspended in the fluid remain as a suspended powder so the suspension can easily be injected through a small needle into the desired body part. Carriers can be selected from non-toxic liquid polymers, liquid surfactants, liquid plasticizers and solvents. Examples of liquid polymers that can be used as a carrier include, but are not limited to, polypropylene glycol, polyethylene glycol, silicone fluid, polyoxyethylene-polyoxypropylene copolymers, stearyl alcohol, lauric acid, and myristic acid. Examples of liquid surfactants that can be used as a carrier in the present invention include, but are not limited to, polysorbate, polyoxyethylene glycol esters of fatty acids, polyoxyethylene ethers. Examples of liquid plasticizers that can be used as carriers in the present invention include, but are not limited to, glycerol, propylene glycol, adipates, amide esters, benzoates, azelates, castor oil, cod liver oil, triethyl citrates, epoxidized vegetable oils, tridecanol ethylene oxide, glyceryl triacetate, glycol esters, glycolates, oleates, penta erythritol fatty acid, ester, polyesters and diethyl succinate. An example of solvents that can be used in the present invention include, but are not limited to, alcohols, valeric acid, caprylic acid and octylacetate.

Although not wanting to be bound by the following hypothesis, the present invention is believed to work in the following manner. The viscoelastic hydrophilic polymers are characteristically thick viscous gels when in an aqueous environment. However, when the dry polymers are ground into a powder or are prepared as beads, they can be suspended in a hydrophobic fluid. The suspension is easily extruded through a fine needle at high concentrations. If necessary, large quantities of the polymers can easily be implanted into a human or animal as dictated by the therapeutic need. Once the polymer suspension is implanted into the body, the non-toxic hydrophobic fluid diffuses away from the polymer as is replaced by aqueous body fluids. The polymer then absorbs or adsorbs water and becomes a viscous fluid that is suitable as a lubricant for a joint or other body part.

Hydrophilic polymers swell or shrink due to changes in their secondary, tertiary and/or quaternary structure. Generally speaking, these changes depend on environmental parameters, such as electric current, ionic strength, pH, exposure to photons, valence of metal ions, concentration of metal ions, hydrophilicity/hydrophobicity of the carrier molecules or hydration level of the polymer.

The preferred concentration of polymer powder in the hydrophobic carrier is between approximately 0.01 and 1 g of polymer per gram of hydrophobic carrier. An especially preferred concentration of polymer powder in the hydrophobic carrier is between approximately 0.05 and 0.5 g of polymer per gram of hydrophobic carrier.

The following specific examples will illustrate several embodiments of the present invention. It will be appreciated that other examples will be apparent to those of ordinary skill in the art and that the invention is not limited to these specific illustrative polymers or carriers.

EXAMPLE 1

0.1 g of chondroitin sulfate (Sigma Chemical Co., St. Louis, Mo.) is suspended in 1 g of glycerol (Sigma Chemical Co., St. Louis, Mo.). The suspension is thoroughly mixed to provide a uniform suspension suitable for use in a human or animal.

EXAMPLE 2

0.1 g of chondroitin sulfate is suspended in 1 g of propylene glycol (Sigma Chemical Co., St. Louis, Mo.). The suspension is thoroughly mixed to provide a uniform suspension suitable for administration to a human or animal.

EXAMPLE 3

0.1 g of chondroitin sulfate is suspended in 1 g of stearyl alcohol (Sigma Chemical Co., St. Louis, Mo.) at 60° C. The suspension is thoroughly mixed to provide a uniform suspension suitable for administration to a human or animal.

EXAMPLE 4

0.1 g of hyaluronic acid (Diagnostic, Minneapolis, Minn.) is suspended in 1 g of glycerol. The suspension is thoroughly mixed to provide a uniform suspension suitable for administration to a human or animal.

EXAMPLE 5

0.1 g of potassium hyaluronic acid is suspended in one gram of propylene glycol. The suspension is thoroughly mixed to provide a uniform suspension suitable for administration to a human or animal.

EXAMPLE 6

0.1 g of sodium hyaluronic acid is suspended in 1 g of myristyl alcohol at 38° C. The suspension is thoroughly mixed to provide a uniform suspension suitable for administration to a human or animal.

EXAMPLE 7

0.1 g of hyaluronic acid is suspended in 1 g of lauric acid U.S.P at 45° C. The suspension is thoroughly mixed to provide a uniform suspension suitable for administration to a human or animal.

EXAMPLE 8

0.1 g of lyophilized human albumin is suspended in 1 g of valeric acid (Sigma Chemical Co., St. Louis, Mo.). The suspension is thoroughly mixed to provide a uniform suspension suitable for administration to a human or animal.

EXAMPLE 9

0. 1 g of lyophilized Arg-Gly-Asp is suspended in 1 g of lauric acid U.S.P at 45° C. The suspension is thoroughly mixed to provide a uniform suspension suitable for administration to a human or animal.

EXAMPLE 10

0.1 g of lyophilized Val-Pro-Gly-Val-Gly is suspended in 1 g of lauric acid U.S.P at 45° C. The suspension is thoroughly mixed to provide a uniform suspension suitable for administration to a human or animal.

EXAMPLE 11

0.1 g of sodium hyaluronic acid is suspended in 1 g of myristic acid at 54° C. The suspension is thoroughly mixed to provide a uniform suspension suitable for administration to a human or animal.

EXAMPLE 12

A suspension of 4 micron beads of lightly cross-linked polyacrylamide suspended in polyethylene glycol can be easily injected through a 30-gauge needle into cutaneous tissues to restore a dent or depressed dermal line. After injection into the body, the beads gradually swell as they equilibrate with body fluid. The four micron beads swell to 40 microns thereby avoiding phagocytosis by macrophages. The fully hydrated beads have a polymer content of less then 0.1% (w/w). The hydrated polymer now acts a lubricant and supplements the body's own natural lubricant.

EXAMPLE 13

A suspension (or paste) of 20 micron beads of polyacrylamide suspended in a polypropylene glycol can be easily injected through a 20 gauge needle into a joint. After injection, the beads gradually swell to 100 microns. The polymer content of the fully hydrated beads is below 0.8% (w/w). The beads are not readily phagocytized by white cells such as macrophages or neutrophils and remain in the joint cavity. After hydration, the polymer acquires physical properties which promote efficient lubrication of the joint surfaces.

EXAMPLE 14

A suspension (or paste) of 150 micron beads of poly(2-hydroxy ethyl methacrylate) suspended in a lauric acid can be easily injected through a 16-gauge needle. After injection, these beads gradually swell to 450 microns. The polymer beads in the tissue is less than 3.7% (w/w).

It should be understood that the foregoing relates only to preferred embodiments of the present invention and that numerous modifications or alterations may be made without departing from the spirit and scope of the invention as set forth in the appended claims.

I claim:

1. A composition for supplementing natural lubricating fluids in a human or animal comprising an effective amount of solid, hydrophilic, synthetic polymer particles suspended by being mixed into a liquid, non-aqueous carrier to form a non-viscous suspension, wherein the composition is essentially free of water, and wherein the particles form a viscous lubricating liquid when injected into the human or animal.

2. The composition of claim 1, wherein the synthetic polymer is selected from the group consisting of methylcellulose, hydroxypropylmethylcellulose, polyacrylonitrile polymer, polyethylene, glycolpolyurethane, hydrophilic polyurethane, polyvinylpropylene, poly(2-hydroxyethyl methacrylate), polyleucine, polylysine, poly(ethylene-vinylalcohol) copolymer, and cross-linked polyvinylpropylene and poly-L-lysine.

3. The composition of claim 2, wherein the synthetic polymer is cross-linked.

4. The composition of claim 1, wherein the polymer is a powder made up of particles.

5. The composition of claim 1, wherein the particles are between approximately 4 microns and 150 microns in diameter.

6. The composition of claim 1, wherein the carrier is selected from the group consisting of polypropylene glycol, polyethylene/glycol, silicone fluid, polyoxyethylene-polyoxypropylene copolymers, glycerol, propylene glycol, adipates, benzoates, azelates, castor oil, cod liver oil, triethyl citrate, epoxidized vegetable oils, tridecanol ethylene oxide, glyceryl triacetate glycolates, oleates, pentaerythritol fatty acid, and diethyl succinate, ethanol, valeric acid, caprylic acid and octylacetate.

7. A method for supplementing natural lubricating fluids in a human or animal comprising injecting into the human or animal an effective amount of solid, hydrophilic, synthetic polymer particles suspended by being mixed into a liquid, non-aqueous carrier to form a non-viscous suspension, wherein the composition is essentially free of water, and wherein the particles form a viscous lubricating liquid when injected into the human or animal.

8. The method of claim 7, wherein the synthetic polymer is selected from the group consisting of methylcellulose, hydroxypropylmethylcellulose, polyacrylonitrile polymer, polyethylene, glycolpolyurethane, hydrophilic polyurethane, polyvinylpropylene, poly(2-hydroxyethyl methacrylate), polyleucine, polylysine, poly(ethylene-vinylalcohol) copolymer, and cross-linked polyvinylpropylene and poly-L-lysine.

9. The method of claim 8, wherein the synthetic polymer is cross-linked.

10. The method of claim 7, wherein the polymer is a powder made up of particles.

11. The method of claim 7, wherein the particles are between approximately 4 microns and 150 microns in diameter.

12. The method of claim 7, wherein the carrier is selected from the group consisting of polypropylene glycol, polyethylene glycol, silicone fluid, polyoxyethylene-polyoxypropylene, copolymers, glycerol, propylene glycol, adipates, benzoates, azelates, castor oil, cod liver oil, triethyl citrate, epoxidized vegetable oils, tridecanol ethylene oxide, glyceryl triacetate glycolates, oleates, pentaerythritol fatty acid, and diethyl succinate, ethanol, valeric acid, caprylic acid and octylacetate.

* * * * *